(12) United States Patent
Kim et al.

(10) Patent No.: US 12,091,699 B2
(45) Date of Patent: Sep. 17, 2024

(54) METHOD FOR ENHANCING PRODUCTION OF HOMEOPROTEIN USING INHIBITOR OF LYSOSOMAL FUNCTION

(71) Applicant: Korea Advanced Institute of Science and Technology, Daejeon (KR)

(72) Inventors: Jin Woo Kim, Daejeon (KR); Jun Woo Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 58 days.

(21) Appl. No.: 17/586,234

(22) Filed: Jan. 27, 2022

(65) Prior Publication Data

US 2022/0243242 A1 Aug. 4, 2022

(30) Foreign Application Priority Data

Feb. 2, 2021 (KR) .................. 10-2021-0014881
Dec. 24, 2021 (KR) .................. 10-2021-0187511

(51) Int. Cl.
*C12P 21/02* (2006.01)

(52) U.S. Cl.
CPC .................. *C12P 21/02* (2013.01)

(58) Field of Classification Search
None
See application file for complete search history.

(56) References Cited

U.S. PATENT DOCUMENTS

| 6,982,252 B2 * | 1/2006 | Paglin ............... C12Q 1/42 424/9.2 |
| 2011/0237497 A1 * | 9/2011 | Xu .................. A61K 31/56 435/375 |

FOREIGN PATENT DOCUMENTS

KR 10-2330387 B1 11/2021

OTHER PUBLICATIONS

Nardo et al., Physiol Rev 98, pp. 1943-1982, 2018.*
Eun Jung Lee et al., "Global Analysis of Intercellular Homeodomain Protein Transfer", Cell Reports, Jul. 16, 2019, pp. 712-722.
Choi Kyeong Sook, "Improvement of TRAIL-based cancer therapy via lysosomal inhibition", Ajou University Industry Academy Cooperation Foundation, Jun. 19, 2012, pp. 1-64.

* cited by examiner

*Primary Examiner* — Richard G Hutson
(74) *Attorney, Agent, or Firm* — Paratus Law Group, PLLC

(57) ABSTRACT

A composition for enhancing the production of a homeoprotein includes an inhibitor of lysosomal function. A method for enhancing the production of a homeoprotein, includes treating cells with an inhibitor of lysosomal function, a method for producing an animal cell line continuously expressing a homeoprotein and a method for mass-producing a homeoprotein using the animal cell line.

2 Claims, 6 Drawing Sheets

METHOD FOR ENHANCING PRODUCTION OF HOMEOPROTEIN USING INHIBITOR OF LYSOSOMAL FUNCTION

CROSS-REFERENCE TO RELATED APPLICATION

This application claims priority to Korean Patent Application No. 10-2021-0014881 (filed on Feb. 2, 2021) and Korean Patent Application No. 10-2021-0187511 (filed on Dec. 24, 2021), which are all hereby incorporated by reference in their entirety.

BACKGROUND

The present invention relates to a method for enhancing the production of a homeoprotein using an inhibitor of lysosomal function, and more particularly, to a composition for enhancing the production of a homeoprotein including an inhibitor of lysosomal function, a method for enhancing the production of a homeoprotein, including: treating cells with an inhibitor of lysosomal function, a method for producing an animal cell line continuously expressing a homeoprotein and a method for mass-producing a homeoprotein using the animal cell line.

A transcription factor is a protein that regulates the transcription process of producing RNA by binding to specific DNA sequences to decrypt genetic information. To perform these essential functions, the transcription factor migrates and is present inside the nucleus containing target DNA.

Among these transcription factors, homeoproteins, which are known to be particularly important in determining cell fate of a development process, are a group of transcription factors having a homeodomain, and are known to have a cytoplasmic function other than an inherent function as a transcription factor in the nucleus. The homeoprotein regulates the translation RNA to protein in the cytoplasm, and such a regulatory process acts as an important factor in the division of body segments in the early embryonic development of *Drosophila*. The homeoprotein that performs the function in the cytoplasm is not only derived endogenously, but foreign homeoproteins secreted from the surrounding neighboring cells may also permeate the cell membrane of the corresponding cell.

The ability of the homeoprotein to move between cells has been recognized to be important not only in a morphological sense but also in terms of developmental physiology. For example, animal visual system established in a development process requires a neuronal maturation process to perform its normal function. In particular, the development of parvalbumin interneuron in the primary visual cortex (V1) is an important for the maturation of vision. Orthodenticle homeobox 2 (Otx2) homeoprotein that acts as a core factor for the development and survival of the parvalbumin interneuron. The Otx2 homeoprotein is usually made and secreted primarily from the choroid plexus of the brain, and migrates through the cerebrospinal fluid to reach the parvalbumin interneurons of the cerebral cortex. Eventually, by regulating the translation process of proteins such as lectins in the cytoplasm of the reached parvalbumin interneurons, Otx2 induces the maturation of parvalbumin interneurons and the construction of a neural network in the V1 cortex (Cell. 2008 Aug. 8; 134(3):386-7). In addition, additional cell migratory homeoproteins are known to play an important physiological role in vivo. Cell permeated ventral anterior homeobox 1 (Vax1) is known to stimulate the growth of retinal ganglion cell axons and engrailed homeobox 2 (En2) is known to enhance mitochondrial function in the dopaminergic neurons.

Based on the physiological role of these migratory homeoproteins, some proteins have been developed as therapeutic agents for Parkinson's disease, Amyotrophic Lateral Sclerosis (ALS), and the like. However, it has been reported that when a homeoprotein is produced by a method using *E. coli*, which has been widely used for protein production, there is a disadvantage in that the production yield is low because aggregation occurs to insolubilize the homeoprotein. Therefore, there is an urgent need for developing a technique capable of producing a homeoprotein structurally intact at high-concentration.

SUMMARY

Based on the aforementioned background, as a result of intensive studies on a method capable of producing a homeoprotein with high efficiency, the present inventors confirmed high production efficiency for the homeoprotein in animal cells manufactured so as to continuously express the homeoprotein, and as a result of treating the cells with an inhibitor of lysosomal function, the present inventors confirmed that both intracellular expression and extracellular secretion levels of the homeoprotein were remarkably increased, thereby completing the present invention.

Thus, an object of the present invention is to provide a composition for enhancing the production of a homeoprotein.

Further, another object of the present invention is to provide a method for enhancing the production of a homeoprotein.

In addition, still another object of the present invention is to provide a method for producing an animal cell line continuously expressing a homeoprotein, and an animal cell line produced by the method.

Furthermore, yet another object of the present invention is to provide a method for mass-producing a homeoprotein.

However, technical problems to be solved by the present invention are not limited to the aforementioned problems, and other problems that are not mentioned may be clearly understood by the person skilled in the art from the following description.

To achieve the aforementioned objects of the present invention, the present invention provides a composition for enhancing the production of a homeoprotein.

As an exemplary embodiment of the present invention, the inhibitor of lysosomal function may be a V-ATPase inhibitor or a lysosomal pH enhancer.

As another exemplary embodiment of the present invention, the V-ATPase inhibitor may be any one selected from the group consisting of bafilomycin A1, bafilomycin D and concanamycin A.

As still another exemplary embodiment of the present invention, the lysosomal pH enhancer may be chloroquine.

As yet another exemplary embodiment of the present invention, the homeoprotein may be any one selected from the group consisting of orthodenticle homeobox 2 (Otx2), engrailed homeobox 2 (En2) and ventral anterior homeobox 1 (Vax1).

Further, the present invention provides a method for enhancing the production of a homeoprotein, the method including: treating a cell expressing a homeoprotein with an inhibitor of lysosomal function.

As an exemplary embodiment of the present invention, the cell may be an animal cell.

In addition, the present invention provides a method for producing an animal cell line continuously expressing a homeoprotein, the method including: preparing an animal cell; introducing an expression vector including a homeobox-containing gene into the animal cell; and selecting the animal cell into which the expression vector is introduced, and then culturing the animal cell for clonal selection.

Furthermore, the present invention provides an animal cell line continuously expressing a homeoprotein, which is produced by the method.

As an exemplary embodiment of the present invention, the expression vector may have the cleavage map of FIG. 1A.

As another exemplary embodiment of the present invention, the expression vector may be introduced into animal cells in a linearized form.

Further, the present invention provides a method for mass-producing a homeoprotein, the method including: treating the animal cell line with an inhibitor of lysosomal function; and obtaining a culture by continuously culturing the cells treated with the inhibitor of lysosomal function.

As an exemplary embodiment of the present invention, the method may be performed in vitro.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1A is the structure of a genetic vector for expressing an Otx2 homeoprotein introduced into HeLa cells, and FIG. 1B is a set of results of analyzing the intracellular expression of Otx2 protein by performing immunocytochemical (ICC) staining on untreated control HeLa cells, Otx2 protein-expressing HeLa cells produced by a transient gene introduction technique from the target DNA and Otx2 protein-expressing HeLa cells produced using a semi-permanent gene introduction technique;

FIG. 2A illustrates the results of analyzing the intracellular expression of Otx2 protein by performing immunocytochemical staining on a control (vehicle) and cells treated with each of BafA1, ConA and CQ, which are inhibitors of lysosomal function, FIG. 2B illustrates the results of each performing a dot blot (DB) analysis and western blot (WB) using cells treated with each of BafA1, ConA and CQ, and FIG. 2C illustrates the results of performing a dot blot (DB) analysis and western blot (WB) after treating the cells with each of BafA1, BafD and ConA, which are inhibitors of lysosomal function, at each concentration and the results of showing the quantitative comparison of the amounts of relatively secreted Otx2 protein.

DETAILED DESCRIPTION

Figure 1A:
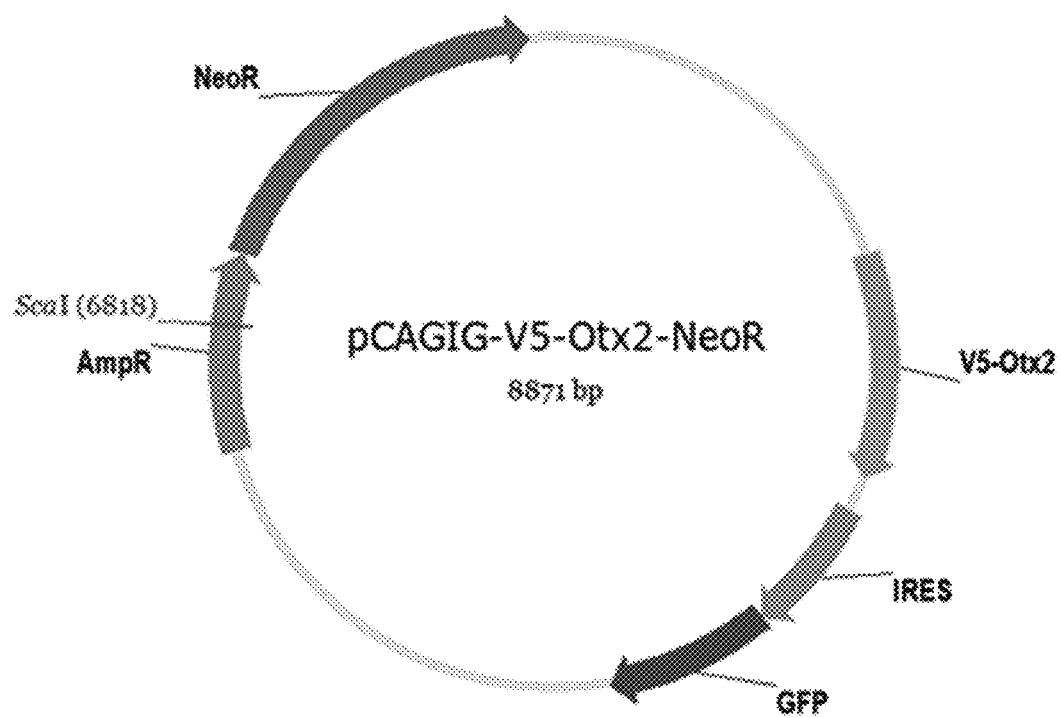
FIGS. 1A and 1B illustrate the results of manufacturing a cell line by introducing a target DNA expressing an Otx2 homeoprotein into HeLa cells by a semi-permanent gene introduction technique in order to manufacture an artificial animal cell that continuously produces a homeoprotein.

Hereinafter, the present invention will be described in detail.

The present invention relates to a platform technology capable of producing a homeoprotein with high efficiency using an animal cell, and it was confirmed that an animal cell expressing a homeoprotein continuously and with a high efficiency was manufactured and the production of the homeoprotein could be induced at a remarkably high level by treating cells expressing the homeoprotein with an inhibitor of lysosomal function, thereby completing the present invention.

Thus, the present invention provides a composition for enhancing the production of a homeoprotein, including an inhibitor of lysosomal function.

As used herein, the term inhibitor of lysosomal function may include all materials capable of inhibiting the degradation of proteins by lysosomes, and the type and action mechanism, and the like of a specific material are not limited as long as the material exhibits the above effect. As a non-limiting example, the inhibitor of lysosomal function in the present invention may be a V-ATPase inhibitor or a lysosomal pH enhancer.

The V-ATPase (vacuolar-ATPase) is a vacuolar type H+ ATPase, and an enzyme having a function of pumping protons. The V-ATPase exhibits various functions in eukaryotic organisms, acidifies many intercellular organelles, and pumps protons across the plasma membrane of various cell types. The enzyme pairs the energy of ATP hydrolysis with the transport of protons. Therefore, the V-ATPase inhibitor, which is the inhibitor of lysosomal function according to the present invention, may exhibit an effect of inhibiting the activity of a hydrolase present in the lysosome by suppressing the function of the V-ATPase to increase the pH in the lysosome. In the present invention, the V-ATPase inhibitor may be any one selected from the group consisting of bafilomycin A1, bafilomycin D and concanamycin A, but is not limited thereto.

In the present invention, the lysosomal pH enhancer may be chloroquine, but is not limited thereto, and the type thereof is not limited as long as it is a material which exhibits the effect of inhibiting the activity of the hydrolase present in the lysosome as described above by increasing the pH in the lysosome.

As used herein, the term "enhancing the production of a homeoprotein" may refer to both an increase in expression level of the homeoprotein in the cell and an increase in extracellular secretion of the homeoprotein.

In the present invention, a technology capable of effectively enhancing the production of a homeoprotein was established by selecting an orthodenticle homeobox 2 (Otx2) protein as an example of the homeoprotein.

In an example of the present invention, in order to produce animal cells which continuously produce the homeoprotein, an Otx2 protein expression vector was manufactured, and DNA obtained by linearizing the vector was semi-permanently inserted into HeLa cells, thereby manufacturing a transformed HeLa cell line which continuously produces an Otx2 protein. As a result of analyzing the expression level of an Otx2 protein in the manufactured cell line by an immunocytochemical staining, it was confirmed that the protein was expressed at a higher level compared to HeLa cells in which the transient expression of the Otx2 protein was induced, and through this, the high production efficiency of the homeoprotein of the manufactured cell line was confirmed (see Example 2).

In another example of the present invention, to investigate the effect of an inhibitor of lysosomal function on the production of a homeoprotein, the production level of the Otx2 protein was analyzed by treating the cells manufactured in Example 2 with various types of inhibitors of lysosomal function at each appropriate concentration and performing immunocytochemical staining, a dot blot analysis and a western blot analysis. As a result, it was confirmed that both intracellular expression and extracellular secretion of the Otx2 protein were remarkably increased when the cells were treated with an inhibitor of lysosomal function, although the degree was different depending on the type of inhibitor of lysosomal function (see Example 3).

Thus, as another aspect of the present invention, the present invention provides a method for enhancing the production of a homeoprotein, the method including: treating a cell expressing a homeoprotein with an inhibitor of lysosomal function.

The homeoprotein may be produced in vitro, and the cell may be an animal cell.

In the present invention, the animal cells may include cells derived from all tissues of an animal, and preferably may be cells derived from mammals, but the type of animal from which the cell is derived, the tissue of origin, and the like are not specifically limited as long as the cells can be transformed by gene introduction and can produce a specific homeoprotein. A method for culturing animal cells may be performed by a known method according to the characteristics of each cell, and culture conditions such as culture medium, temperature, concentration of carbon dioxide, culture container, and culture time are not specifically limited, and can be appropriately set by those skilled in the art.

Thus, as still another aspect of the present invention, the present invention provides a method for producing an animal cell line continuously expressing a homeoprotein, the method including: preparing an animal cell; introducing an expression vector including a homeobox-containing gene into the animal cell; and selecting the animal cell into which the expression vector is introduced, and then culturing the animal cell for clonal selection.

Furthermore, the present invention provides an animal cell line continuously expressing a homeoprotein, which is produced by the method.

In the present invention, the expression vector may be an expression vector having the cleavage map illustrated in FIG. 1A of the present invention, but the type and configuration thereof are not specifically limited as long as it is a vector that can be introduced such that a target homeobox-containing gene can be continuously expressed in cells.

In the present invention, the introducing of the expression vector including the homeoprotein into the animal cell may be performed by transforming the cell using a semi-permanent gene introduction technique, and in the present invention, the expression vector may be introduced into the animal cell in a linearized form to be inserted into a genome of the cell, but the method is not limited thereto. The transformed cell means continuously producing a target protein while the corresponding animal cell is cultured rather than transiently expressing a gene.

As used herein, the term "transformation" means that a gene can be introduced into a host cell to allow the gene to be expressed in the host cell. In the present invention, for transformation, a gene may be introduced into eukaryotic cells to be transformed preferably by a known method such as transient transfection, microinjection, transduction, cell fusion, calcium phosphate precipitation, liposome-mediated transfection, DEAE dextran-mediated transfection, polybrene-mediated transfection, and electroporation, but the method is not limited thereto.

The clonal selection may be appropriately selected and applied by those skilled in the art as long as it is a method of selecting only cells into which a gene has been introduced in the art, and in the present invention, clonal selection may be preferably performed using the antibiotic resistance of the cells into which the expression vector has been introduced, and more preferably, the antibiotic may be neomycin, but is not limited thereto.

Further, as yet another aspect of the present invention, the present invention provides a method for mass-producing a homeoprotein, the method including: treating the animal cell line with an inhibitor of lysosomal function; and obtaining a culture by continuously culturing the cells treated with the inhibitor of lysosomal function.

In the present invention, the method of treating the cells with an inhibitor of lysosomal function may be preferably performed by adding the inhibitor to a culture medium of cells and culturing the cells in the medium.

In the present invention, in order to obtain a homeoprotein from the cells treated with the inhibitor of lysosomal function, after a cell culture solution is obtained while continuously culturing the cells, a desired homeoprotein may be isolated from a culture supernatant, purified, and recovered.

A method of recovering the homeoprotein is not particularly limited, and the homeoprotein may be obtained by concentrating a culture supernatant obtained by centrifuging a culture in which the cells treated with the inhibitor of lysosomal function are cultured, and subjecting the culture supernatant to a known purification method.

In addition, as yet another aspect of the present invention, the present invention provides a use of a composition for enhancing the production of a homeoprotein for use in the mass-production of the homeoprotein.

Furthermore, as yet another aspect of the present invention, the present invention provides a use of the animal cell line for use in the mass-production of the homeoprotein.

Further, as yet another aspect of the present invention, the present invention provides a use of a homeoprotein produced by the animal cell line for use in the manufacture of a medicine for preventing or treating Parkinson's disease.

Further, as yet another aspect of the present invention, the present invention provides a use of a homeoprotein produced by the animal cell line for use in the manufacture of a medicine for preventing or treating Parkinson's disease.

As used herein, the term "Parkinson's disease" refers to a degenerative brain disease of the nervous system caused by the loss of dopaminergic neurons. Resting tremor, rigidity, bradykinesia (bradypragia) and postural instability characteristically appear, and it is generally known that clinical symptoms begin to appear after the age of 60.

As used herein, the term "prevention" refers to all actions that suppress or delay the progression of Parkinson's disease by administering the composition for promoting the differentiation of neural stem cells into dopaminergic neurons and neural stem cells.

As used herein, the term "treatment" refers to all actions that alleviate or beneficially change Parkinson's disease by administering the composition for promoting the differentiation of neural stem cells into dopaminergic neurons and neural stem cells.

In addition, as yet another aspect of the present invention, the present invention provides a use of a homeoprotein produced by the animal cell line for use in the manufacture of a medicine for preventing or treating an optic nerve disease.

Hereinafter, preferred examples for helping the understanding of the present invention will be suggested. However, the following examples are provided only to more easily understand the present invention, and the contents of the present invention are not limited by the following examples.

EXAMPLES

Example 1. Experimental Materials and Experimental Methods

1-1. Manufacture of Otx2 Protein Expression Cell Line

In order to construct an animal cell that continuously produces an Otx2 protein, the present inventors semi-permanently inserted genetic information into the animal cell, and the specific process is as follows.

(1) Manufacture of Otx2 protein expression gene: In order to manufacture a gene expressing an Otx2 protein, as illustrated in FIG. 1A, a vector into which an Otx2 gene with a V5 peptide marker sequence (V5-Otx2) and a neomycin antibiotic resistance gene (NeoR) had been inserted, was used. Since the vector has only one Sca1 restriction enzyme action sequence, a circular plasmid DNA vector can be made into linear DNA using a Sca1 restriction enzyme.

(2) Introduction of Otx2 protein expression gene into cells: The linearized DNA is advantageous for semi-permanent insertion into the genomic information of cells. Thus, after the vector illustrated in FIG. 1A, which was manufactured as described above using a Sca1 restriction enzyme, was made into linear DNA, the linearized DNA was introduced into HeLa cells by a lipid transfection technique.

(3) Selection of cells into which Otx2 protein expression gene has been introduced: In order to select only individual HeLa cells into which an Otx2 gene had been introduced from the transfected HeLa cells, the G418 compound, which is a functional equivalent of a neomycin antibiotic, was added to a cell culture solution at a concentration of 500 μg/mL. Since the vector illustrated in FIG. 1A has a neomycin antibiotic resistance gene (NeoR) inserted therein, cells show normal growth even after treatment with the G418 compound, otherwise, cells are removed because apoptosis is induced. As a result, continuous exposure to a medium including the G418 compound allows only cells into which an Otx2 gene resistant to the G418 compound has been introduced to be selected. The cells into which the Otx2 gene was introduced were selected by culturing the HeLa cells into which the DNA was introduced for 30 days while exchanging the cell culture solution to which the G418 compound was added at 2-day intervals.

1-2. Immunocytochemistry

Cells were cultured on a cover glass in a cell incubator for 24 hours or more, and treated with a fixing solution (physiological saline including 4% paraformaldehyde) at room temperature for 20 minutes to fix the cells. Next, after the cells were treated with a permeability-imparting solution (physiological saline including 0.1% TWEEN-20 (polysorbate 20)) at room temperature for 10 minutes, the cells were treated with a blocking solution (physiological saline including 10% donkey serum) at room temperature for 1 hour. Subsequently, the cells were treated with a blocking solution including a primary antibody, cultured at 4° C. for 16 hours, then treated with a blocking solution 10 including a fluorophore-conjugated secondary antibody, and cultured at room temperature for 1 hour. Then, the fluorescence signals of the cells were analyzed under an Olympus FV1000 confocal microscope.

1-3. Dot Blot Analysis

In order to detect a homeoprotein secreted to the outside of the cell, a cell culture solution including sodium heparin was allowed to pass through a polyvinylidene difluoride (PVDF) membrane. Next, the membrane was treated with a blocking solution (TBST including 5% skim milk) and allowed to react at room temperature for 1 hour. Subsequently, the membrane was treated with a blocking solution including a primary antibody, allowed to react at 4° C. for 16 hours, then treated with a horseradish peroxidase (HRP)-conjugated secondary antibody, and cultured at room temperature for 1 hour, and then the membrane was exposed to an X-ray photosensitive film by inducing an enzymatic reaction using an ECL solution as a substrate to thereby analyze the results.

1-4. Western Blot Analysis

In order to detect a homeoprotein present inside the cell, cells were lysed with a RIPA lysate (tertiary distilled water including 20 mM Tris-HCl, pH 7.5, 150 mM NaCl, 1 mM $Na_2EDTA$, 1 mM EGTA, 1% NP-40, 1% sodium deoxycholate, 2.5 mM sodium pyrophosphate, 1 mM β-glycerophosphate, 1 mM $Na_3VO_4$, and 1 μg/ml leupeptin), and then proteins in the cells were separated according to molecular weight by performing electrophoresis (SDS-PAGE) on the cell lysate on a polyacrylamide gel including sodium dodecyl sulfate. The gel was induced to electrically bind to a PVDF membrane after protein separation to transfer the proteins to the membrane. Next, the membrane was treated with a blocking solution (TBST including 5% skim milk), allowed to react at room temperature for 1 hour, subsequently treated with a blocking solution including a primary antibody, allowed at 4° C. for 16 hours, then treated with a horseradish peroxidase (HRP)-conjugated secondary antibody, and cultured at room temperature for 1 hour, and then the membrane was exposed to an X-ray photosensitive film by inducing an enzymatic reaction using an ECL solution as a substrate to thereby analyze the results.

Example 2. Manufacture of Artificial Animal Cell for Production of Homeoprotein The present inventors intended to construct an animal cell that continuously produces a homeoprotein, and as an example, manufactured a cell that produces an Otx2 homeoprotein using HeLa, a human-derived uterine cancer cell line. For this purpose, an Otx2 homeoprotein expression vector having the structure illustrated in FIG. 1A was introduced into HeLa cells according to the method of Example 1-1. Then, immunocytochemical staining was performed on the cells selected as having the vector introduced thereinto according to the method of Example 1-2 in order to confirm whether the homeoprotein was expressed.

Figure 1B:
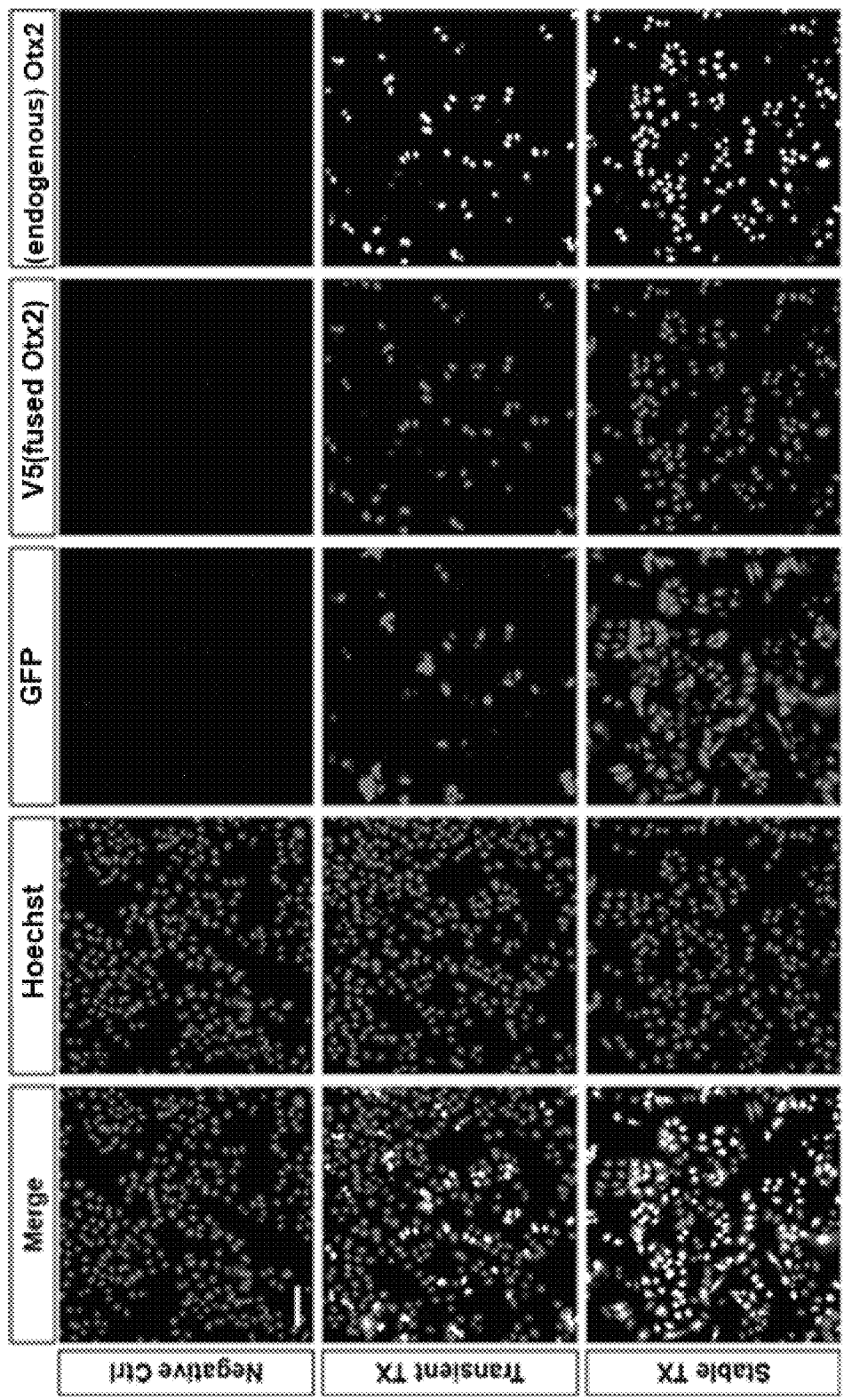

As a result, as illustrated in FIG. 1B, it was confirmed that the Otx2 protein was not expressed in the case of the original HeLa cells (Negative Ctrl), which were not treated at all, in the first row, and in cells (Transient TX) into which the vector had been introduced using a gene introduction technique in the second row, it was observed that the Otx2 protein was expressed, but the production efficiency was somewhat low. However, in cells manufactured using a semi-permanent gene introduction technique in the third row, the Otx2 protein was observed to be expressed, and high production efficiency compared to cell density was confirmed.

Example 3. Confirmation of Enhanced Expression of Otx2 Homeoprotein by Treatment with Inhibitor of Lysosomal Function The present inventors predicted that homeoproteins are proteins that act in the nucleus and are degraded by proteasomes like most nuclear proteins, but confirmed that a considerable number of homeoproteins migrated to the lysosome and were degraded, contrary to the prediction. Since the lysosome fuses with a cell membrane and secretes internal materials to the outside of the cell according to the cell environment, the present inventors expected, based on this phenomenon, that when the secretion of the homeoprotein by the lysosome was suppressed and simultaneously, the fusion of the lysosome with the cell membrane was promoted, the secretion of the homeoprotein would be increased.

Accordingly, the present inventors treated a HeLa cell line that continuously produces the Otx2 homeoprotein manufactured in Example 2 with a V-ATPase inhibitor and a lysosomal pH enhancer as inhibitors of lysosomal function, and confirmed a change in secretion of the homeoprotein. The V-ATPase inhibitor is a lysosomal ion channel inhibitor, and when cells are treated with the inhibitor, the pH in the lysosome is increased, so the protein degradation by the lysosome may be suppressed because the activity of the hydrolase present in the lysosome is inhibited.

Thus, specifically, after the HeLa cells were treated with each of V-ATPase inhibitors bafilomycin A1 (BafA1) and concanamycin A (ConA), and a lysosomal pH enhancer chloroquine (CQ) at different concentrations for 16 hours, the intracellular expression of the Otx2 protein was observed by immunocytochemical staining.

Figure 2A:
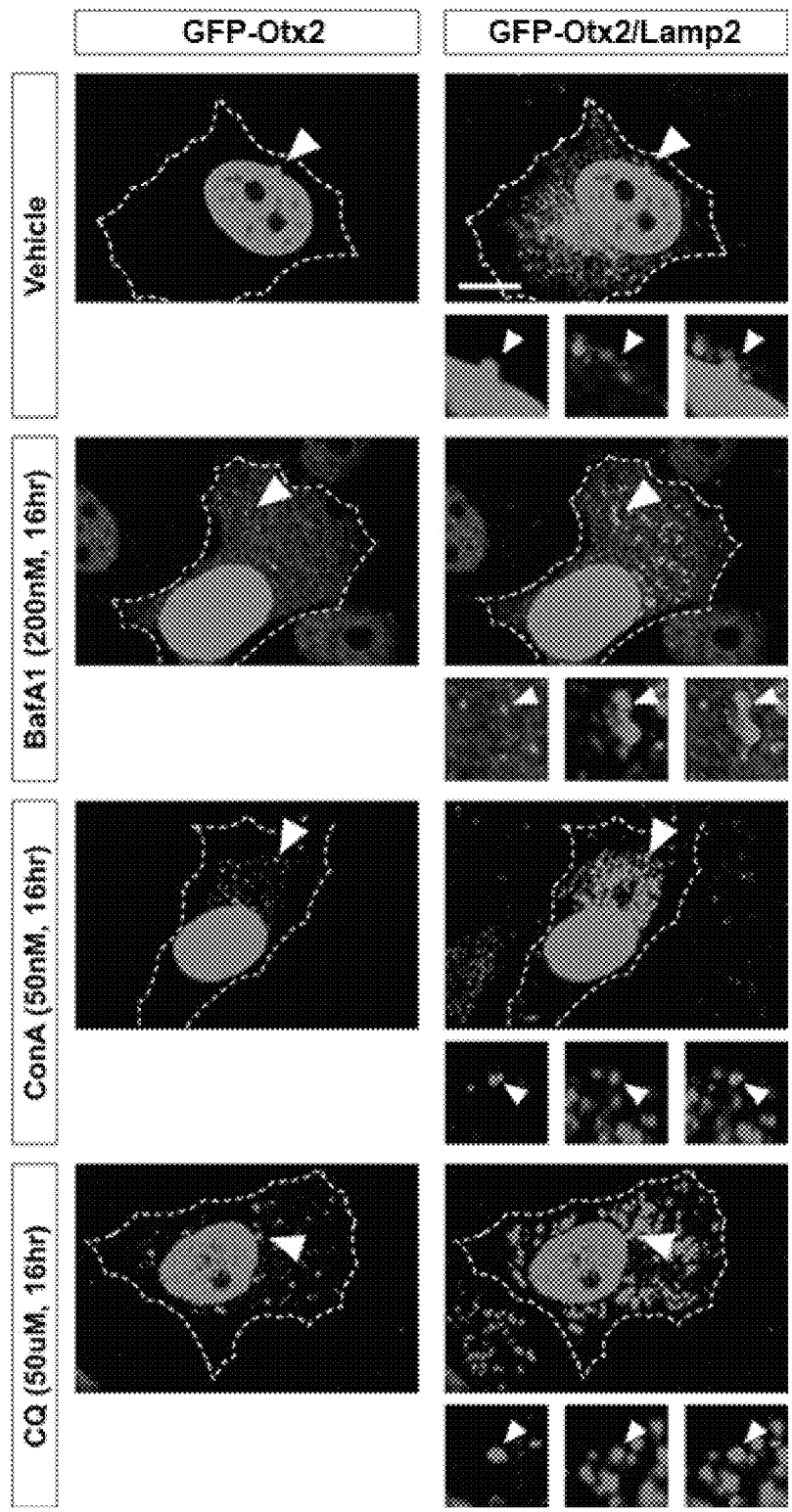
FIGS. 2A-2C illustrate the results of analyzing Otx2 protein levels outside and inside the cells after treating HeLa cells manufactured so as to produce an Otx2 homeoprotein with an inhibitor of lysosomal function.

As a result, as illustrated in FIG. 2A, in the case of a control (vehicle) treated with only a dilution solvent of the inhibitor of lysosomal function, the Otx2 protein was almost exclusively observed in the cell nucleus, meaning that an intracellular position of a cell nucleus protein Otx2 is a normal expression pattern that is usually characterized by the cell nucleus. In contrast, it was confirmed that the expression pattern of Otx2 commonly occurred even in the cytoplasm including the cell nucleus in groups treated with each of inhibitors of lysosomal function BafA1, ConA and CQ compounds.

Figure 2B:
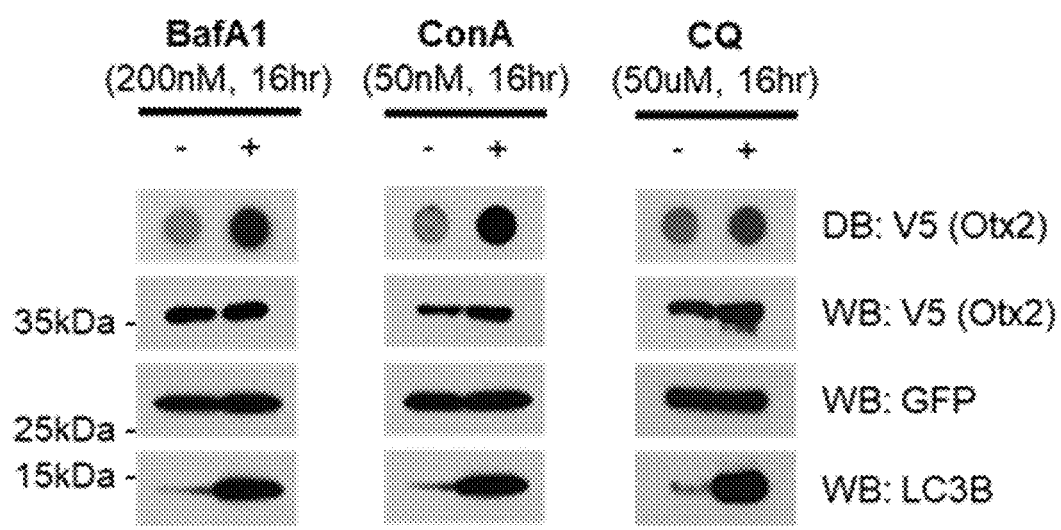

Furthermore, the level of secreted Otx2 protein and the intracellular expression level of Otx2 protein when the HeLa cells were treated with the inhibitor of lysosomal function were analyzed by a dot blot analysis and a western blot analysis. As a result, as illustrated in FIG. 2B, DB in the first row: V5 (Otx2) is a result showing the level of Otx2 protein detected in a cell culture solution, which is an external environment of the cell, showing that when the cells were treated with each inhibitor of lysosomal function (+), the extracellular secretion of the protein was remarkably increased. WB in the second row: the V5 (Otx2) result is a result showing the expression level of the Otx2 protein in a cell lysate, which is an internal environment of the cell, and when the cells were treated with BafA1, a big difference did not appear, but it was found that when the cells were treated with ConA or CQ, the Otx2 protein was expressed at a higher level.

The third row of FIG. 2B shows the expression level of a GFP protein detected in a cell lysate, although side effects of the inhibitor of lysosomal function for proteins other than the Otx2 protein were confirmed, it could be seen that there were no side effects by treatment with the inhibitor of lysosomal function by observing that the expression levels were constant in all the groups. The last row is a result of confirming the level of an LC3B (LC3II) protein, which is an autophagy marker, the validity of the inhibitor of lysosomal function was confirmed by an increase in LC3B protein during the treatment with the inhibitor of lysosomal function.

Figure 2C:
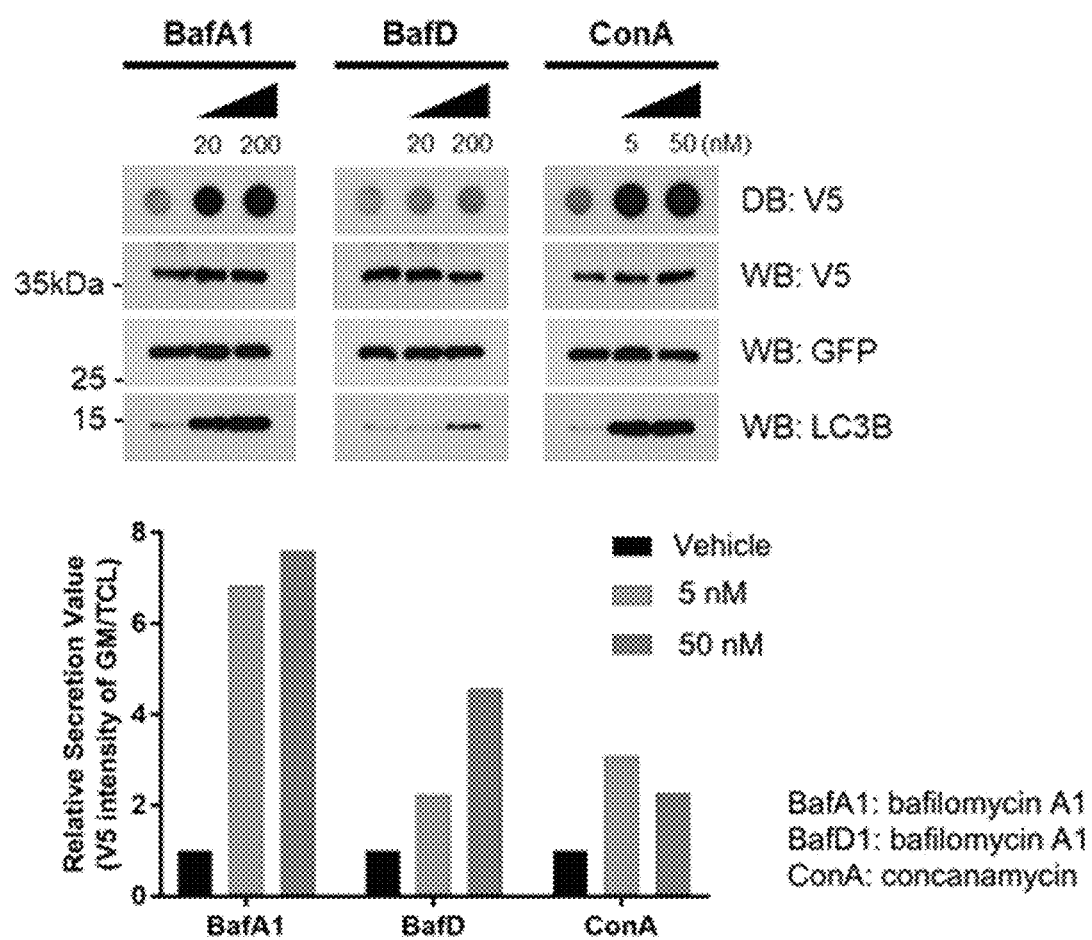

In addition, the present inventors treated the HeLa cells with bafilomycin D (BafD) together with bafilomycin A1 (BafA1) and concanamycin A (ConA), which are types of V-ATPase inhibitors, at different concentrations, and performed an analysis in the same manner as in FIG. 2B. As a result, as illustrated in FIG. 2C, it was confirmed that as the concentrations of the inhibitors increased from 20 nM to 200 nM or the concentration of ConA was increased from 5 nM to 50 nM, the secretion of the Otx2 protein to the outside of the cell and the intracellular expression of the protein were increased.

Additionally, changes in secretion of a Vax1 protein and an En2 protein and changes in expression of the proteins were observed in order to verify the validity of effects of the inhibitors of lysosomal function for different types of homeoproteins.

Figure 3:
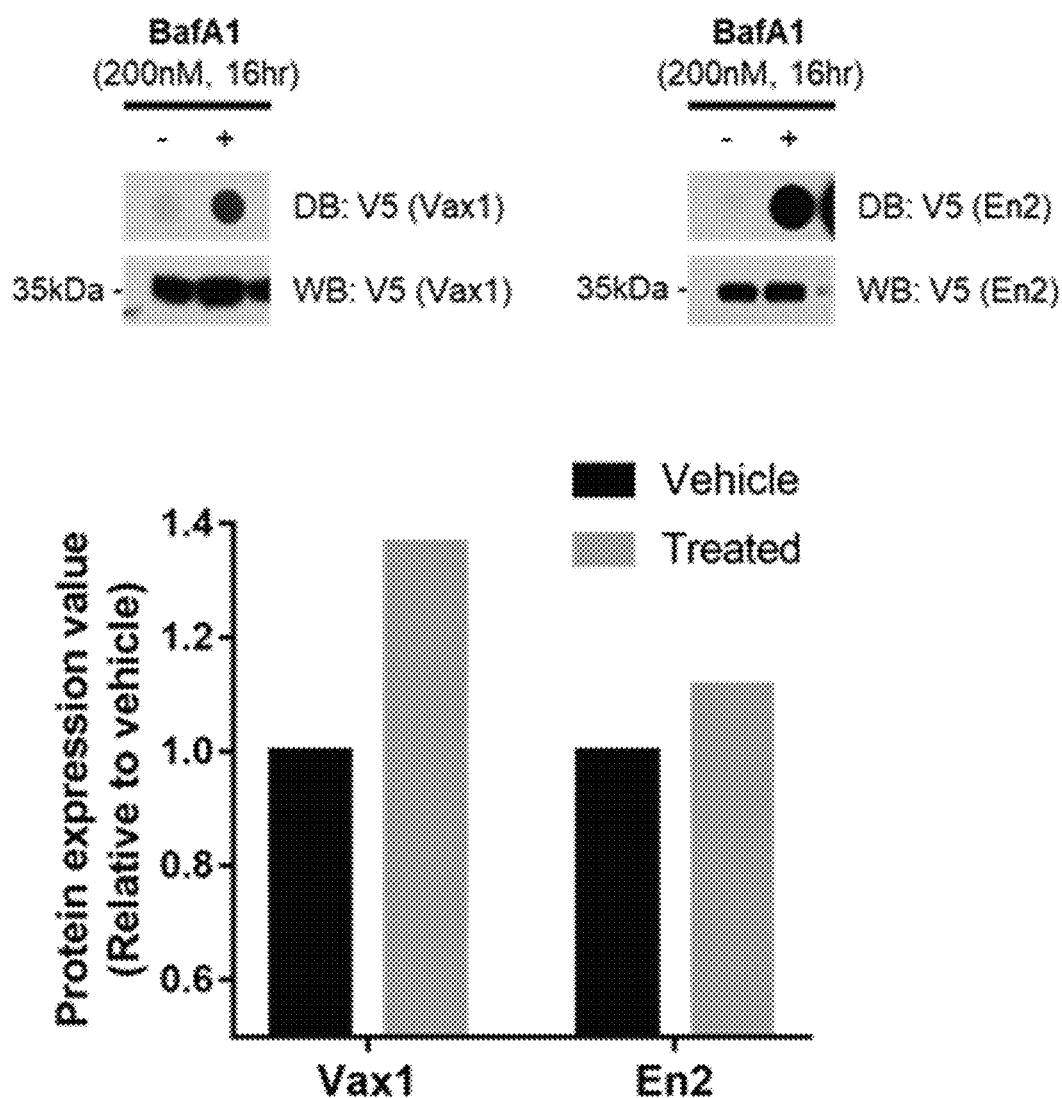
FIG. 3 illustrates the results of respectively performing a dot blot (DB) analysis and western blot (WB) in order to analyze the protein levels outside and inside the cells after treating cells expressing Vax1 and En2 homeoproteins with an inhibitor of lysosomal function BafA1.

As a result, as illustrated in the results of FIG. 3, it was confirmed that when cells were treated with an inhibitor of lysosomal function, both Vax1 and En2 proteins showed the same pattern as the pattern confirmed for the Otx2 protein.

Through the results of the above examples, it could be seen that when animal cells continuously expressing a homeoprotein were treated with an inhibitor of lysosomal function, the intracellular expression and extracellular secretion of the homeoprotein were remarkably enhanced.

According to the present invention, as a result of comparing expression levels of a specific homeoprotein by manufacturing an animal cell line continuously expressing the homeoprotein, it was confirmed that a protein production rate was remarkably higher compared to transient protein expression, and that when the cells were treated with an inhibitor of lysosomal function, the intracellular expression of a homeoprotein and the secretion of the homeoprotein to the outside of the cells were remarkably increased. Thus, a desired homeoprotein can be mass-produced with high efficiency by treating animal cells continuously expressing the homeoprotein with an inhibitor of lysosomal function and continuously culturing the animal cells, so the present invention is expected to be usefully utilized as a protein production platform in the field of therapeutic agent development using various homeoproteins.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

What is claimed is:

1. A composition for enhancing production of a homeoprotein, comprising an inhibitor of lysosomal function and an animal cell into which has been introduced an expression vector comprising a homeobox encoding gene;
   wherein the inhibitor of lysosomal function is a V-ATPase inhibitor or a lysosomal pH enhancer;
   wherein the V-ATPase inhibitor is any one selected from the group consisting of bafilomycin A1, bafilomycin D and concanamycin A;
   wherein the lysosomal pH enhancer is chloroquine, and wherein the homeoprotein is any one selected from the group consisting of orthodenticle homeobox 2 (Otx2), engrailed homeobox 2 (En2) and ventral anterior homeobox 1 (Vac1).

2. The composition of claim 1, wherein the animal cell is a HeLa cell.

* * * * *